United States Patent [19]

Palestrant

[11] Patent Number: 5,002,528
[45] Date of Patent: Mar. 26, 1991

[54] PERCUTANEOUS IRRIGATION AND DRAINAGE SYSTEM

[76] Inventor: Aubrey Palestrant, 6800 N. 47th St., Paradise Valley, Ariz. 85253

[21] Appl. No.: 451,470

[22] Filed: Dec. 15, 1989

[51] Int. Cl.[5] .............................................. A61M 1/00
[52] U.S. Cl. ..................................... 604/28; 604/246; 604/30; 604/54
[58] Field of Search ....................... 604/19, 21, 27-35, 604/246, 248, 264, 280-283, 258, 49, 54.93; 137/625.47, 625.41, 606, 597

[56] References Cited

U.S. PATENT DOCUMENTS

| | | |
|---|---|---|
| 1,683,723 | 9/1928 | Myres . |
| 2,644,450 | 7/1953 | Krewson ............................. 128/218 |
| 2,860,636 | 11/1958 | Seitchik et al. ...................... 128/227 |
| 3,329,147 | 7/1967 | Barron ................................ 128/230 |
| 3,750,668 | 8/1973 | Perl .................................... 128/227 |
| 3,848,603 | 11/1974 | Throner ............................... 128/349 |
| 4,157,717 | 6/1979 | Goldberg ............................. 604/32 |
| 4,219,021 | 8/1980 | Fink .................................... 128/214 |
| 4,306,976 | 12/1981 | Bazzato ............................... 604/29 |
| 4,525,156 | 6/1985 | Benusa et al. ....................... 604/28 |
| 4,581,011 | 4/1906 | Campbell ............................ 604/29 |
| 4,585,435 | 4/1986 | Vaillancourt ........................ 604/27 |
| 4,704,102 | 11/1987 | Guthery .............................. 604/28 |
| 4,902,282 | 2/1990 | Bellotti et al. ....................... 604/246 |
| 4,950,230 | 8/1990 | Kendell ............................... 604/28 |

OTHER PUBLICATIONS

Pruett T. L., Simmons R. L. (1988) "Status of Percutaneous Catheter Drainage of Abscesses", *Surg. Clin. North Am.* 68: 89–105.
Kaye W. (1982) "Catheter and Infusion-Related Sepsis: The Nature of the Problem and its Prevention", *Heart Lung*, 11:221-228.
"The NAMIC Protection Station", promotional brochure dated Nov. 1988, *NAMIC Angiographics Systems Division.*
VanSonnenberg E., Ferrucci J. T., Jr., Mueller P. R., Wittenberg J., Simeone J. F.: "Percutaneous Drainage of Abscesses and Fluid Collections: Techniques, Results and Applications", *Radiology* 1982: 142: 1-20.
Lang E. K., Springer R. M., Gloriose III L. W., Cammarata C. A.: "Abdominal Abscess Drainage Under Radiologic Guidance: Causes of Failure", *Radiology 1986;* 159: 329-336.
Mueller P. R., VanSonnenberg E., Ferrucci, Jr.; J. T.: "Percutaneous Drainage of 250 Abdominal Abscesses and Fluid Collections", *Radiology 1984;* 151: 343-347.

*Primary Examiner*—C. Fred Rosenbaum
*Assistant Examiner*—Kathleen A. Daley
*Attorney, Agent, or Firm*—Cahill, Sutton & Thomas

[57] ABSTRACT

A closed system for percutaneous irrigation and drainage of cavities containing abscesses, sterile fluid collections or hematomas includes an irrigant reservoir; an irrigation tube connects the reservoir to a first port of a first three-ported connector adapted to fluidically connect two of the three ports at a time. A syringe is connected to the second port of the first connector, and an extension tube connects the third port of the first connector to a first port of a second three-ported connector adapted to fluidically connect two of the three ports at a time. The distal end of a drainage catheter is adapted to be placed in the cavity. The proximal end of the catheter is connected to the second port of the second connector. A drainage tube is connected to the third port of the second connector to a means for collecting fluids draining from the cavity.

9 Claims, 2 Drawing Sheets

PERCUTANEOUS IRRIGATION AND DRAINAGE SYSTEM

FIELD OF THE INVENTION

This invention relates to a closed system for percutaneous irrigation and drainage of abscesses, sterile fluid collections or hematomas.

DESCRIPTION OF THE PRIOR ART

Percutaneous drainage of abscesses using CT, ultrasound or fluoroscopic guidance is in widespread clinical practice. Placement of drainage catheters percutaneously avoids the need for an operation on a patient who is ill: the risks associated with percutaneous drainage are far smaller than the risk of surgery. A variety of placement techniques and catheters have been used for this procedure. The sizes of catheters used are relatively small, some measuring no more than 3 or 4 mm. in diameter. These catheters are used to remove the liquid within the abscess or cavity and also to remove solid debris. A common problem with such catheters occurs when drainage holes in the catheter becomes blocked by debris too large to pass through the holes. Therefore, it is well known by those familiar with the art that for drainage to be successful, the catheters need to be flushed on a regular basis to insure catheter patency and function by opening the drainage holes, to thin the abscess fluid, and to facilitate breakup of debris into particles small enough to pass through the drainage holes.

For adequate drainage of abscesses, it is therefore necessary that drainage catheters be irrigated at frequent intervals, for example, three or four times a day. Catheter irrigation typically requires several steps. First, a syringe is filled with irrigant from a sterile source. Next, the catheter is disconnected from the drainage bag, the syringe is connected to the catheter, and the catheter is flushed with irrigant. Finally, the catheter is reconnected to the drainage bag. Alternatively, a three way stopcock can be used between the drainage catheter and the drainage tubing. To flush the catheter, a syringe filled with irrigant is connected to the third port of the stopcock, fluid is injected, and the syringe is removed. This method is expensive and time consuming since it requires new syringes, needles and irrigant sources each time the catheter is flushed.

This technique for flushing catheters may cause nosocomal infections, however, because three way stopcocks and connections may become contaminated with micro-organisms from the hands of personnel or from the syringe during the frequent irrigations. The possibility of contamination may be compounded by the failure to treat the stopcock with strict aseptic techniques or to keep a sterile cap on the irrigation port of the stopcock when not in use. Therefore, each time a connection to the stopcock is undone, there is a potential for contamination of the abscess by outside micro-organisms. It is likely that the larger the number of connections and disconnections, the higher the risk of contamination.

It is also important to contain the drained infected material within a collection system. This is especially true when there is aggressive irrigation and drainage, such as when the abscess is first entered and there is aspiration of the infected material followed by liberal irrigation. At that time, it is possible that infected material may splatter onto staff or be disseminated into the air.

Situations may be encountered where it is important to prevent contamination of a cavity. For example, a catheter may be placed percutaneously into a cavity for fluid collection without it being immediately apparent that infection is present. Such situations occur when a catheter is passed into a sterile hematoma or serous fluid collections. Culture of the collected fluid may take several days; during that time it is important not to introduce infection into a sterile cavity.

Sometimes a cavity may contain a blood clot (hematoma). The clot may be liquified and drained by irrigating the cavity with thrombolytic drugs such as urokinase. In this situation it would be important to prevent the cavity from becoming contaminated until all the blood clot is removed and the cavity collapses.

A further problem relates to adequate cavity drainage. Those familiar with the art believe that gentle suction is advantageous to encourage drainage of fluid and to facilitate removal of debris through the drainage holes in the catheter. This suction is often supplied by connecting the drainage catheter to wall suction. Such a connection often restricts the patient to his bed; if the patient wishes to ambulate, suction must be disconnected, therefore interrupting drainage of the cavity.

Accordingly, it is an object of the present invention to provide an inexpensive closed irrigation and drainage system which, when connected at the time of percutaneous insertion of the drainage catheter anywhere in the body, remains connected until the cavity is drained and healed; at no time must any component be disconnected, except to periodically replenish the irrigant source.

It is another object of the present invention to provide a means for rapidly and forcefully injecting a fixed amount of irrigant such as saline or medications into a cavity to dilute the liquid therein and to facilitate break up of large pieces of debris or blood clot into particles small enough to pass through the catheter.

It is another object of the present invention to provide a closed irrigation and drainage system for percutaneous cavity drainage which can maintain sterile conditions while connected to a percutaneous drainage catheter until the contents of the cavity has drained out or the cavity is healed.

It is another object of the present invention to provide continuous gentle suction using the siphon effect created by placement of the drainage bag below the level of the drained cavity.

SUMMARY OF THE INVENTION

Briefly described, and in accordance with one embodiment thereof, the present invention relates to a percutaneous system for irrigating and draining an abscess, sterile fluid collection or hematoma. The system includes an irrigant reservoir; an irrigation tube connects the reservoir to a first port of a first three-ported connector adapted to fluidically connect two of the three ports at a time. A syringe is connected to the second port of the first connector, and an extension tube connects the third port of the first connector to a first port of a second three-ported connector adapted to fluidically connect two of its three ports at a time. The distal end of a catheter is adapted to be placed in the abscess. The opposing proximal end of the catheter is coupled to the second port of the second connector. A drainage tube is connected between the third port of the second connector and a means for collecting fluids draining from the abscess.

In a preferred embodiment of the present invention, the first and second three ported connectors are three way stopcocks. Fluids draining from the cavity are collected in a collection bag positioned below the level of the catheter so as to facilitate the siphoning of the irrigation fluid from the catheter to the drainage bag.

To irrigate the catheter, the first three-way stopcock is adjusted to fluidically connect its first and second ports, thereby establishing a flow passage from the reservoir to the syringe. A pre-determined volume of irrigant is drawn into the syringe. Next, the first stopcock is adjusted to fluidically connect its second and third ports, and the second stopcock is adjusted to fluidically connect its first and second ports, thus establishing a flow passage between the syringe and the catheter. The syringe is then operated to expel the irrigant, which travels through the flow passage established by manipulating the two stopcocks, and flushes the catheter. To allow spent irrigant and debris to drain from the cavity, the second stopcock is adjusted to fluidically connect its second and third ports, thus establishing a flow passage between the catheter and the drainage bag.

DETAILED DESCRIPTION OF THE PREFERRED EMBODIMENTS

Figure 1:
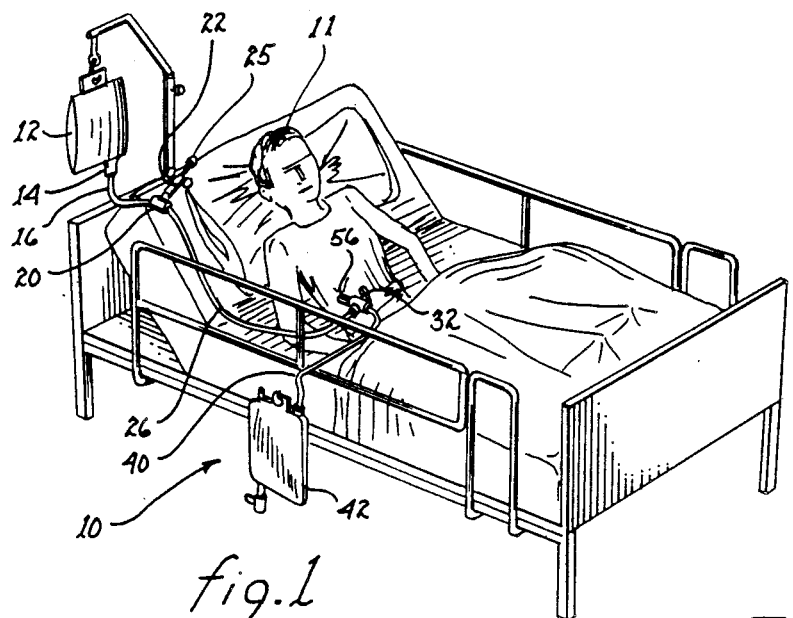
FIG. 1 is a perspective view of a percutaneous irrigation and drainage system of the present invention shown in use on a patient.
Figure 2:
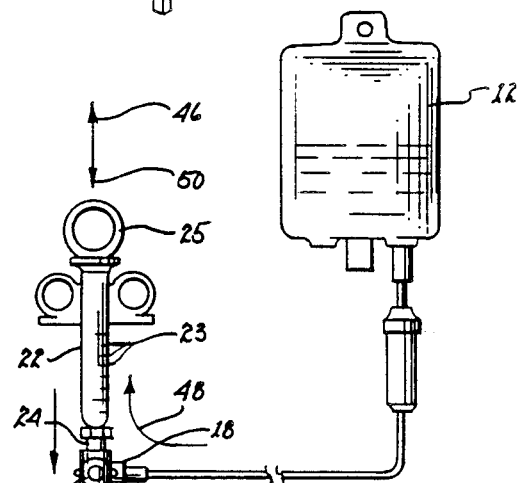
FIG. 2 is a schematic view of the percutaneous irrigation and drainage system of FIG. 1.
Figure 2:
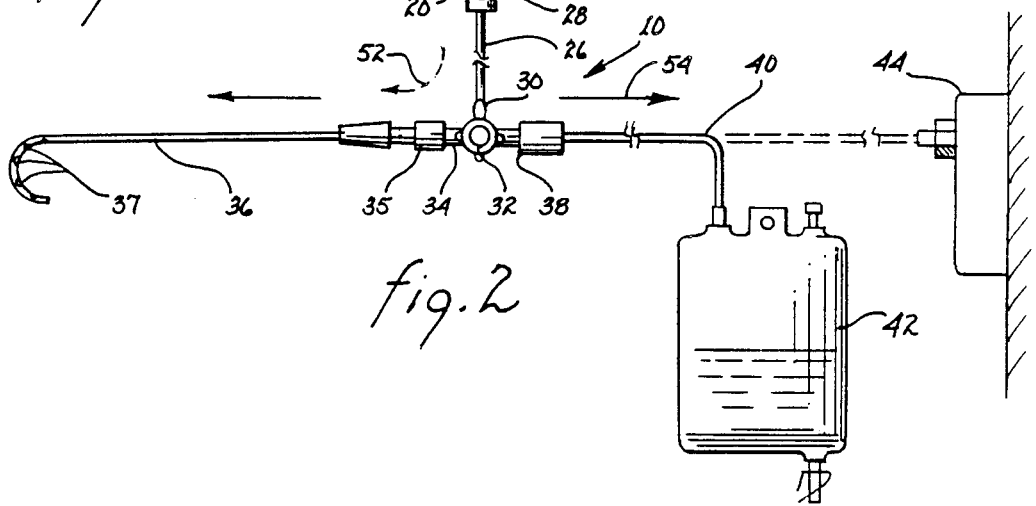
Figure 4:
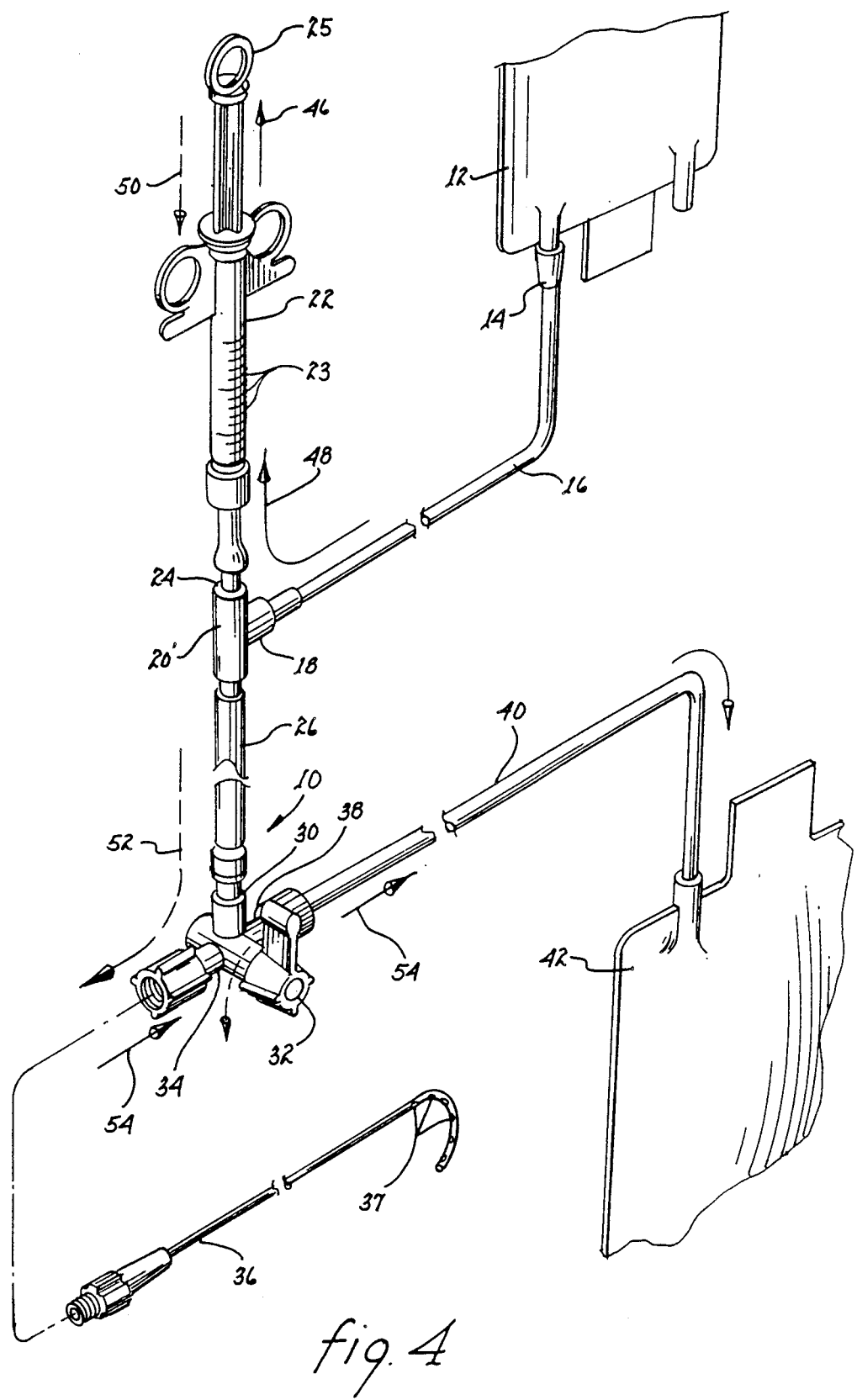
FIG. 4 is a perspective view of a percutaneous irrigation and drainage system like that of FIG. 1, but wherein a valved three-ported connector is substituted for a stopcock.

In FIG. 1, a percutaneous irrigation and drainage system designated generally by reference numeral 10 is shown in use on bedridden patient 11. FIGS. 2 and 4 show system 10 in more detail. Referring generally to FIGS. 1, 2 and 4, system 10 includes an irrigant reservoir 12, preferably an IV bag containing a standard volume (typically, 100 cc) of saline solution or other irrigant. Attached to reservoir 12 is infusion chamber 14 so that flow from the reservoir may be observed. Irrigation tube 16 connects chamber 14 to a first port 18 of a first three-way stopcock 20 adapted to fluidically connect two of the three ports at a time. A luer lock syringe 22, having volume graduations 23 marked thereon and a plunger 25, is connected to a second port 24 of first stopcock 20.

One end of extension tubing 26 is connected to a third port 28 of stopcock 20; the other end of tubing 26 is connected to a first port 30 of a second three-way stopcock 32; as with first stopcock 20, the second stopcock is adapted to fluidically connect two of the three ports of the second stopcock at a time. A second port 34 of second stopcock 32 is connected to the proximal end of catheter 36 at its connector 35; catheter 36 contains drainage holes 37 in its opposing distal end. Catheter 36 is typically a 5.5, 7 or 8.5 French trocar type drainage catheter. A third port 38 of second stopcock 32 is connected to one end of drainage tubing 40; the other end of tubing 40 is connected to drainage bag 42.

As shown in FIG. 1, drainage bag 42 is located below the level of the patient to promote suction of drainage fluids into the bag by a siphon effect. If stronger suction is necessary, drainage tubing 40 can be connected to a wall-mounted collection chamber 44 as shown in FIG. 2, coupled to a plumbed vacuum line (not shown) located behind the wall.

The manner of percutaneous irrigation and drainage of a cavity using system 10 will now be described with reference to FIGS. 1–4. Catheter 36 is placed inside an abscess, sterile fluid collection, or hematoma (not shown) of patient 11 by means of C.T., ultrasound or fluoroscopic guidance. Cavities to be drained are typically situated in an intra-abdominal, retroperitoneal, pelvic or plural location. After placement of catheter 36, fluid is aspirated from the cavity to shrink the cavity as much as possible.

To irrigate the abscess and flush catheter 36, first threeway stopcock 20 is adjusted to fluidically connect its first port 18 and second port 24, thereby establishing a flow passage between reservoir 12 and syringe 22: syringe plunger 25 is pulled upward in the direction shown by arrow 46 to a syringe volume gradation 23 equal to the desired volume of irrigant; upward movement of the plunger causes irrigant to flow into syringe 22 from reservoir 12 in the direction shown by arrow 48. The particular irrigant volume will depend on the size of the cavity, but should not exceed half of the volume initially aspirated from the cavity. Typically, the irrigant volume will be in the range of 5–10 cc.

To allow the irrigant to flow from syringe 22 into catheter 26, first stopcock 20 is adjusted to fluidically connect its second port 24 to third port 28, and second stopcock 32 is adjusted to fluidically connect its first port 30 to second port 34, thus establishing a flow passage between syringe 22 and catheter 36. Plunger 25 is then depressed in the direction shown by arrow 50, thereby causing irrigant to flow from syringe 22 through first and second stopcocks 20 and 32, respectively, into catheter 36. The irrigant should be injected rapidly in order to clear debris such as necrotic material or blood clots from catheter drainage holes 37.

To allow spent irrigant and debris to drain from the cavity through catheter 36 for ultimate collection in drainage bag 42, second stopcock 32 is adjusted to fluidically connect its second port 34 to third port 38. The direction of drainage flow is indicated by arrow 54. Drainage bag 42 is placed below the level of catheter 36 to facilitate siphoning of drainage fluids from the catheter into the drainage bag. The siphon effect generates suction equivalent to the effective height of a fluid column between drainage holes 37 and drainage bag 42 without the need of the patient to be connected to wall suction. If the patient wishes to ambulate, drainage bag 42 can be attached to the bottom of the patient's gown, thereby maintaining suction even when the patient is not in bed. If stronger suction is required, drainage tubing 40 can be connected to wall-mounted collection chamber 44 (see FIG. 2) which is connected to a vacuum system (not shown) located behind the wall.

At the time of initial placement of catheter 36, the abscess is thoroughly irrigated and drained until there is substantial clearing of the fluid flowing down through drainage tubing 40. A dressing (not shown) is then applied to the patient's skin entry site 56; second stopcock 32 (the drainage stopcock) with attached tubing may be fixed to the skin with adhesive. With the exception of periodically changing the irrigant when reservoir 12 is empty, none of the elements comprising system 10 are removed or changed until the patient's abscess is cured or the hematoma is liquified and drained. Therefore, the possibility of cross-contamination is theoretically eliminated. This is especially important at the time of initial drainage when it may not be known whether the fluid collection is sterile or infected. A gram stain may not reliably exclude infection and a complete culture of e fluid may take several days. During this time, the cavity can be irrigated and drained by closed system 10 of the present invention with minimal risk of contamination. When system 10 is used to drain pleural fluid, a pneumothorax is unlikely because the system is closed and there is not a source of air to be sucked into the pleural cavity. Furthermore, closed system 10 prevents spatter of infected material onto staff or dissemination into the air at the time of placement of catheter 36 when the abscess is aspirated and liberally irrigated.

Referring again to FIGS. 2 and 4, first stopcock 20 may, if desired, be replaced by a three-ported connector (designated 20' in FIG. 4) which includes a pair of one-way valves. The first one-way valve permits fluid to flow from irrigation tube 16 into first port 18 and out second port 24 into syringe 22 when plunger 25 is withdrawn, but precludes fluid flow in the opposite direction when plunger 25 is depressed. The second one-way valve permits fluid to flow from syringe 22 into second port 24 and out third port 28 when plunger 25 is depressed, but which precludes fluid from flowing into third port 28 from extension tubing 26 into syringe 22 when plunger 25 is withdrawn. Such three-ported connectors having valves capable of operating in the above-described manner are commercially available from North American Instrument Corporation of Glen Falls, N.Y., as part of the "NAMIC Protection Station" sold by the NAMIC Angiographic Systems Division under Catalog No. 64000930.

Figure 3:
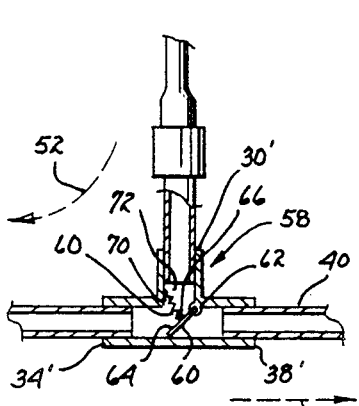
FIG. 3 is another embodiment of a three-ported connector which may be used in the percutaneous irrigation and drainage system of the present invention.

FIG. 3 illustrates an alternative to second stopcock 32. Reference numeral 58 refers generally to a three-port flapper valve; numerals referring to the three ports 30', 34', 38', respectively, are as described above with reference to second stopcock 32. Flap 60 is hinged to corner 62 between first port 30' and third port 38'. Connected to an upper face 64 of flap 60 is a first end 66 of a spring 68. The second end 70 of spring 68 is connected to a wall 72 of first port 30', which wall is opposite corner 62. When irrigant flows from syringe 22 in the direction shown by arrow 52, the force of the fluid will push flap 60 down, extending spring 68, thereby fluidically connecting first port 30' and second port 34', and closing off third port 38' so that irrigant cannot flow into drainage tubing 40. When the flow of irrigant ceases, spring 68 releases, causing flap 60 to be pulled upward, thereby closing off first port 30' and fluidically connecting second port 34' and third port 38' so that drainage fluid can flow from catheter 36 into drainage tubing 40 in the direction shown by arrow 54.

The system and method of the present invention results in a substantial saving in nursing time and cost of materials. In most hospitals, the drainage catheter is flushed two or three times a day using new syringes, needles and bottles of irrigant each time, incurring a considerable cost. Additional time must be allocated by nursing staff to procure these items, draw up the irrigant and flush the catheter. To prevent cross-contamination, hospital policy may dictate that nursing staff use gloves if drainage catheters are frequently manipulated, with the closed irrigation and drainage system of the present invention, such materials are not necessary, resulting in the saving of materials and nursing time during the treatment period which may range from a few days to several weeks.

The system of the present invention can be used with many different types of single lumen drainage catheters. While the drainage catheter is preferably a single-lumen trocar catheter, it may also be a dual lumen sump catheter or other multiple-lumen catheter. Sump catheters cause air to be drawn into the drainage tubing resulting in the cessation of suction from the siphon be connected directly to wall suction.

Those skilled in the art will appreciate that, while a stopcock may be used as a three-ported connector in practicing the present invention, a simple T-connector may also be used, in which case, tubing clamps may be selectively clamped or released from tubes connected to such T-connectors in order to permit fluid flow through the desired ports of the T-connector. Those skilled in the art will also appreciate that, while a syringe has been described for injecting irrigant into the catheter, an automated pump or other powered device may be substituted for such a syringe if desired, and would function equally well.

While the present invention has been described in accordance with a preferred embodiment thereof, the description is for illustrative purposes only and should not be construed as limiting the scope of the invention. Various changes and modifications may be made by those skilled in the art without departing from the true spirit and scope of the invention as defined by the appended claims.

I CLAIM:

1. A percutaneous system for irrigating and draining a cavity containing an abscess, sterile fluid collection, hematoma or the like, the system comprising in combination:

(a) an irrigant reservoir;
   (b) a first three-ported connector having first, second, and third ports, and adapted to fluidically connect two of its three ports at a time;
   (c) first coupling means for coupling the reservoir to the first port of the first connector;
   (d) a syringe connected to the second port of the first connector:
   (e) a second three-ported connector having first, second, and third ports, and adapted to fluidically connect two of its three ports at a time;
   (f) second coupling means for coupling the third port of the first connector and the first port of the second connector;
   (g) a catheter having a distal end adapted to be placed in the cavity, and having an opposing proximal end;
   (h) third coupling means for coupling the proximal end of the catheter to the second port of the second connector; and
   (i) collection means for collecting fluids draining from the cavity, said collection means being coupled to the third port of the second connector.

2. The system of claim 1 wherein the catheter is a trocar type drainage catheter having drain holes adjacent the distal end thereof.

3. The system of claim 2 wherein the first and second three-ported connectors are three-way stopcocks.

4. The system of claim 2 wherein the second three-ported connector includes means for selectively closing the third port of the second connector when irrigant is injected into the catheter, and selectively opening the third port of the second connector when irrigant is not being injected into the catheter.

5. The system of claim 3 wherein the collection means is a drainage bag positioned below the level of the catheter so as to facilitate the siphoning of drainage fluids from the catheter to the drainage bag.

6. The system of claim 3 wherein the drainage fluid collection means comprises a wall mounted collection container and a vacuum line connected to the container so as to positively aspirate drainage fluids from the catheter to the container.

7. A method for percutaneously irrigating and draining a cavity containing an abscess, sterile fluid collection, hematoma, or the like, the method comprising the steps of:

(a) supplying irrigation fluid from an irrigant reservoir to a first port of a first three-ported connector adapted to fluidically connect two of its three ports at a time;

(b) coupling a syringe to a second port of the first connector;

(c) coupling the third port of the first connector to a first port of a second three ported-connector adapted to fluidically connect two of its three ports at a time;

(d) coupling the third port of the second connector to a collection container:

(e) installing a distal end of a catheter in the cavity, the distal end of the catheter having drainage holes therein;

(f) coupling a proximal end of the catheter to a second port of the second connector;

(g) configuring the first connector to fluidically connect the first and second ports of the first connector, thereby establishing a flow passage between the irrigation tube and the syringe;

(h) withdrawing a preselected volume of the irrigation fluid from the irrigant reservoir to the syringe:

(i) configuring the first connector to fluidically connect the second and third ports of the first connectors, thereby establishing a flow passage between the syringe and the second connector;

(j) configuring the second connector to fluidically connect the first and second ports of the second connector, thereby establishing a flow passage between the syringe and the catheter;

(k) forcefully expelling the irrigation fluid from the syringe, thereby causing the irrigation fluid to flow into the catheter to irrigate the catheter and adjacent cavity;

(l) configuring the second connector to fluidically connect the first and second ports of the second connector, thereby establishing a flow passage between the catheter and the collection container; and (m) draining fluid from the cavity through the catheter into the collection container.

8. The method of claim 7 wherein the draining step is accomplished by positioning a collection bag below the level of the catheter so as to create a siphon effect between the catheter and the bag.

9. The method of claim 7 wherein the step of coupling the third port of the second connector to a collection container includes the step of coupling the third port of the second connector to a wall-mounted collection chamber connected to a vacuum system to positively aspirate fluid from the cavity into the collection chamber.

* * * * *